US00PP25381P3

(12) United States Plant Patent
Egger

(10) Patent No.: US PP25,381 P3
(45) Date of Patent: Mar. 24, 2015

(54) ***AGASTACHE* PLANT NAMED 'KUDOS MANDARIN'**

(50) Latin Name: ***Agastache* hybrid**
Varietal Denomination: Kudos Mandarin

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 120 days.

(21) Appl. No.: 13/986,506

(22) Filed: May 9, 2013

(65) Prior Publication Data

US 2014/0338088 P1 Nov. 13, 2014

(51) Int. Cl.
*A01H 5/00* (2006.01)

(52) U.S. Cl.
USPC ..... Plt./399

(58) Field of Classification Search
CPC ..... A01H 5/02
USPC ..... Plt./399
See application file for complete search history.

(56) References Cited

PUBLICATIONS

Greenhouse Growers. Terra Nova Nurseries Introduces *Agastache* Kudos Series, (Nov. 21, 2012) retrieved on Oct. 28, 2014, retrieved from the Internet at <www.greenhousegrower.com/varieties/terra-nova-nurseries-introduces-agastache-kudos-series/> 2 pp.*

* cited by examiner

*Primary Examiner* — June Hwu
(74) *Attorney, Agent, or Firm* — Klarquist Sparkman, LLP

(57) ABSTRACT

A new and distinct form of *Agastache* plant characterized by orange flowers in large, dense inflorescences, a long bloom time, a very short, compact habit, good winter hardiness, and excellent vigor.

1 Drawing Sheet

Botanical denomination: *Agastache* hybrid.
Variety designation: 'Kudos Mandarin'.

BACKGROUND OF THE INVENTION

The present invention relates to a new and distinct cultivar of *Agastache*, given the name, 'Kudos Mandarin'. *Agastache* is in the family Lamiaceae. This new variety is one of several selections of new *Agastache* using hardy and dwarf *Agastache* species in the breeding lines to provide hardiness and compactness. The new cultivar is a selection from the cross between the proprietary seedlings *Agastache* 46-1 (unpatented), as the seed parent, and *Agastache* 08-2T (unpatented), as the pollen parent. The new cultivar was selected for its compact habit, hardiness, and orange flowers in dense heads.

Compared to the seed parent, *Agastache* 46-1 the new cultivar is shorter and hardier.

Compared to the pollen parent, *Agastache* 08-2T, the new cultivar has large, orange flowers rather than small light pink flowers.

Compared to *Agastache aurantiaca* 'Orange Sprite' (an unpatented plant), the new cultivar is hardier with darker orange flowers in denser flower heads.

Compared to *Agastache* Orange Nectar™ (unpatented), the new cultivar has clear orange rather than red orange flowers and is more compact and hardier.

This plant exhibits the following characteristics that make it unique:

1. orange flowers in large, dense inflorescences,
2. a long bloom time,
3. a very short, compact habit, 4. good winter hardiness,
5. and excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the new cultivar grown in a one gallon container in full sun in Canby, Oreg.

FIG. 2 shows a group of nine-month-old *Agastache* 'Kudos Mandarin' growing in the field in mid-summer in Canby, Oreg.

DETAILED PLANT DESCRIPTION

The following is a detailed description of the new *Agastache* cultivar based on observations of 6-month-old specimens in early May growing in a gallon container in a warm greenhouse in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5th edition.

Plant:

*Form.*—Upright.

*Type.*—Herbaceous perennial.

*Cold hardiness.*—USDA Zone 6-10.

*Size.*—Grows to 35 cm wide and 38 cm tall to the top of the flowers.

*Vigor.*—Excellent.

*Branching.*—About 20 main stems from the base, these branch at every node.

*Stem.*—Square in cross section, grows to 5 mm wide and 20 cm tall to the first flower, pubescent, internodes range from 0.5 to 3 cm long, Yellow Green 146B.

*Roots.*—White 155B, fibrous, plants root easily from stem tip cuttings.

Leaf:

*Type.*—Simple.

*Arrangement.*—Opposite.

*Shape.*—Ovate.

*Venation.*—Pinnate.

*Margins.*—Crenate.

*Apex.*—Acute.

*Base.*—Truncate to reniform.

*Blade size.*—Grows to 45 mm long and 32 mm wide.

*Surface texture.*—Pubescent on both sides.

*Petiole description.*—4 mm long and 1 mm wide, pubescent, Yellow Green 146A.

*Leaf color.*—Top side Green N137B with vein Green 137B, bottom side closest to Yellow Green 147B with vein 147C.

*Fragrance.*—Aromatic.

Inflorescence:

*Type.*—Terminal spike with up to 7 whorls.

*Number of flowers.*—Up to 100 per spike.

*Size of inflorescence.*—Grows to 11 cm tall and 7 cm wide.

*Peduncle.*—Grows to 5 cm tall and 3 mm wide, pubescent, Yellow Green 146B.

*Pedicel.*—Grows to 1.5 mm long, pubescent, Yellow Green 148C.

*Bloom period.*—June through frost in Canby, Oreg.

Flower bud:

*Size.*—26 mm long and 5 mm wide at the widest point prior to opening.

*Description.*—Tubular.

*Surface texture.*—Pubescent.

*Color.*—Closest to Orange Red 31B.

Flower:

*Type.*—Zygomorphic.

*Shape.*—Bilabiate, tubular.

*Size.*—40 mm long and 9 mm wide.

*Corolla description.*—16 mm long and spreads to 7 mm wide; color outside and inside Orange 26B except lobes inside and bottom lobe both sides Orange Red 31B; glabrous inside, pubescent outside; tube 26 mm long and 1 mm to 5 mm wide; 2 upper lobes joined 5 mm long and 4 mm wide, each oblong, tips acute, margin entire; three lower lobes, two spreading sideways and curve out slightly, each 4 mm long and 4 mm wide, tip acute, margin entire; bottom lobe cupped, orbicular, margin notched, 4.5 mm wide and 4.5 mm long.

*Calyx description.*—Campanulate, 6 mm long and 2 mm wide, pubescent outside and glabrous inside, 5 lobed, lobes triangular, 1 mm long, entire, acuminate, Yellow Green 148C.

*Pistil description.*—33 mm long; ovary 1 mm long, Yellow Green 146D; style 32 mm long, White NN155B blending to Purple 77A on top 6 mm, stigma two-parted, Purple 77A.

*Stamen description.*—4 in number, paired and exerted, top two 11 mm long and bottom two 10 mm long, filaments Purple 77D, anthers 1 mm long, Purple 77C, pollen White N155A.

*Fragrance.*—Aromatic.

*Lastingness.*—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as shown and described.

* * * * *

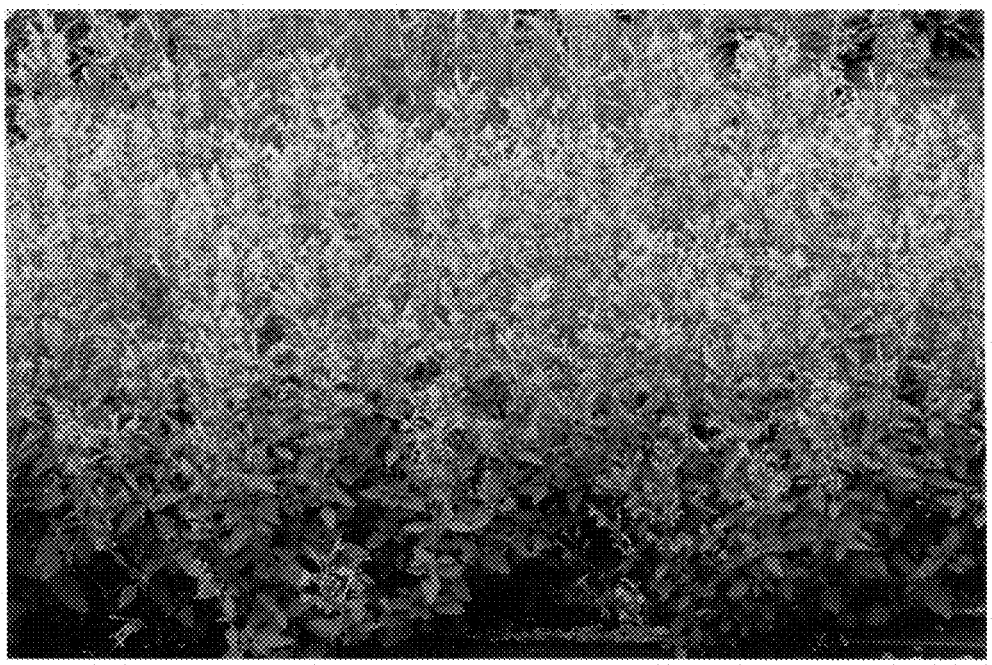

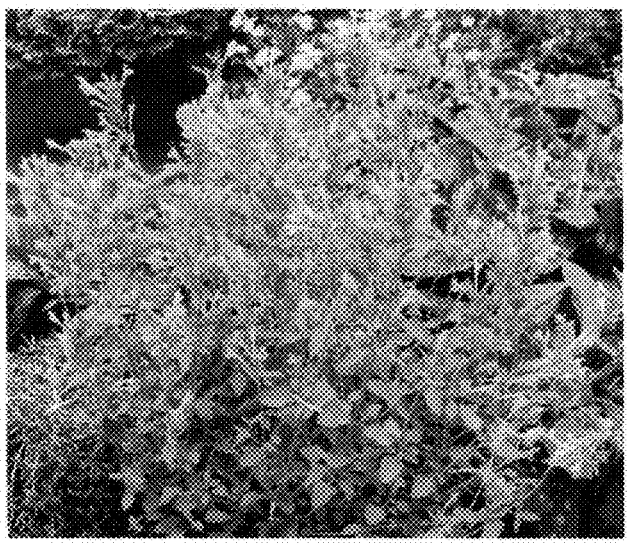
FIG. 1 above, FIG. 2 below